US011471421B2

(12) United States Patent
Bleich Kimelman et al.

(10) Patent No.: US 11,471,421 B2
(45) Date of Patent: Oct. 18, 2022

(54) PROCESS FOR PREPARING MICROPARTICLES CONTAINING GLATIRAMER ACETATE

(71) Applicant: MAPI PHARMA LTD., Ness Ziona (IL)

(72) Inventors: Nadav Bleich Kimelman, Tel Aviv (IL); Shai Rubnov, Tel Aviv (IL); Ehud Marom, Tel Aviv (IL)

(73) Assignee: MAPI PHARMA LTD., Ness Ziona (IL)

( * ) Notice: Subject to any disclaimer, the term of this patent is extended or adjusted under 35 U.S.C. 154(b) by 743 days.

(21) Appl. No.: 16/328,572

(22) PCT Filed: Aug. 28, 2017

(86) PCT No.: PCT/IL2017/050954
§ 371 (c)(1),
(2) Date: Feb. 26, 2019

(87) PCT Pub. No.: WO2018/042423
PCT Pub. Date: Mar. 8, 2018

(65) Prior Publication Data
US 2021/0299057 A1    Sep. 30, 2021

Related U.S. Application Data

(60) Provisional application No. 62/380,426, filed on Aug. 28, 2016.

(51) Int. Cl.
*A61K 9/50* (2006.01)
*A61K 9/00* (2006.01)
*A61K 9/19* (2006.01)

(52) U.S. Cl.
CPC .......... *A61K 9/5094* (2013.01); *A61K 9/0019* (2013.01); *A61K 9/19* (2013.01); *A61K 9/5031* (2013.01)

(58) Field of Classification Search
CPC ...... A61K 9/5094; A61K 9/0019; A61K 9/19; A61K 9/5031
See application file for complete search history.

(56) References Cited

U.S. PATENT DOCUMENTS

| 5,945,126 A | * | 8/1999 | Thanoo | A61K 9/1647 424/425 |
| 5,981,589 A | | 11/1999 | Konfino et al. | |
| 6,048,898 A | | 4/2000 | Konfino et al. | |
| 6,054,430 A | | 4/2000 | Konfino et al. | |
| 6,342,476 B1 | | 1/2002 | Konfino et al. | |
| 6,362,161 B1 | | 3/2002 | Konfino et al. | |
| 6,620,847 B2 | | 9/2003 | Konfino et al. | |
| 7,199,098 B2 | | 4/2007 | Konfino et al. | |
| 8,377,885 B2 | | 2/2013 | Marom et al. | |
| 8,796,226 B2 | | 8/2014 | Marom et al. | |
| 9,200,114 B2 | | 12/2015 | Marom et al. | |
| 2006/0276390 A1 | | 12/2006 | Aharoni et al. | |
| 2008/0063687 A1 | | 3/2008 | Chou et al. | |

FOREIGN PATENT DOCUMENTS

| CN | 1398584 A | 2/2003 |
| CN | 103169670 A | 6/2013 |
| WO | 2005009333 A2 | 2/2005 |
| WO | 2011080733 A1 | 7/2011 |
| WO | 2018042415 A1 | 3/2018 |
| WO | 2018178973 A1 | 10/2018 |

OTHER PUBLICATIONS

Abate et al., Lab Chip, 2011, 11, 1713. (Year: 2011).*
Miller et al., "Glatiramer acetate depot (extended-release) phase lla one-year study in patients with relapsing remitting multiple sclerosis: safety, tolerability and efficacy (NEDA) analysis". 7th Joint ECTRIMS—ACTRIMS Meeting Oct. 25-28, 2017, Paris, France. Abstract; 2 pages.
Miller et al., "Glatiramer acetate depot (extended-release) phase lla one-year study in patients with relapsing remitting multiple sclerosis: safety, tolerability and efficacy (NEDA) analysis". 7th Joint ECTRIMS—ACTRIMS Meeting Oct. 25-28, 2017, Paris, France. Poster; 1 page.
Tiwari and Verma (2011) Microencapsulation technique by solvent evaporation method (Study of effect of process variables). Int J of Pharm & Life Sci (IJPLS) 2(8): 998-1005.
O'Donnell and McGinity (1997) Preparation of microspheres by the solvent evaporation technique. Adv Drug Deliv Rev 28(1): 25-42.

* cited by examiner

*Primary Examiner* — Robert S Cabral
(74) *Attorney, Agent, or Firm* — Rothwell, Figg, Ernst & Manbeck, P.C.

(57) ABSTRACT

The present invention provides an improved process for preparing microparticles containing glatiramer acetate having low levels of residual organic solvent(s), in particular dichloromethane. The microparticles are incorporated into long acting parenteral pharmaceutical compositions in depot form that are suitable for subcutaneous or intramuscular implantation or injection, and that may be used to treat multiple sclerosis.

19 Claims, No Drawings

PROCESS FOR PREPARING MICROPARTICLES CONTAINING GLATIRAMER ACETATE

CROSS REFERENCE TO RELATED APPLICATION

This application is a 35 U.S.C. 371 National Phase Entry Application from PCT/IL2017/050954, filed Aug. 28, 2017, which claims the benefit of U.S. Provisional Patent Application No. 62/380,426 filed on Aug. 28, 2016, the disclosures of which are incorporated herein in their entirety by reference.

FIELD OF THE INVENTION

The present invention relates to an improved process for preparing microparticles containing glatiramer acetate having low levels of residual organic solvent(s), in particular dichloromethane (DCM). The microparticles are incorporated into long acting parenteral pharmaceutical compositions in depot form that are suitable for subcutaneous or intramuscular implantation or injection, and that may be used to treat multiple sclerosis.

BACKGROUND OF THE INVENTION

Glatiramer acetate (GA), marketed under the tradename Copaxone®, is indicated for the treatment of patients with relapsing-forms of multiple sclerosis. Glatiramer acetate is a random polymer composed of four amino acids that are found in myelin basic protein. Glatiramer acetate comprises the acetate salts of polypeptides containing L-glutamic acid, L-alanine, L-tyrosine and L-lysine. The average molar fractions of the amino acids are 0.141, 0.427, 0.095 and 0.338, respectively, and the average molecular weight of copolymer-1 is between 5,000 and 9,000 daltons. Chemically, glatiramer acetate is designated L-glutamic acid polymer with L-alanine, L-lysine and L-tyrosine, acetate (salt). Its structural formula is: (Glu, Ala, Lys, Tyr)x$CH_3COOH$, approx. ratio $Glu_{14}Ala_{43}Tyr_{10}Lyz_{34}$x$(CH_3COOH)_{20}$.

Copaxone® is manufactured as a solution for subcutaneous injection. Each 1 mL of Copaxone® solution contains 20 mg or 40 mg of glatiramer acetate and 40 mg of mannitol. The 20 mg/mL strength is indicated for daily injection, while the 40 mg/mL strength is indicated for injection three times per week. Side effects generally include a lump at the injection site (injection site reaction), aches, fever, and chills.

U.S. Pat. Nos. 8,377,885 and 8,796,226 describe long acting parenteral compositions of pharmaceutically acceptable salts of glatiramer, including glatiramer acetate, in depot form suitable for subcutaneous or intramuscular implantation or injection. The long acting compositions provide equal or superior therapeutic efficacy compared with daily injectable Copaxone® formulations, with reduced incidence and/or severity of side effects such as injection site irritation, due to the reduced frequency of administration. The compositions are prepared by a "double emulsification" process. An aqueous solution of glatiramer acetate is dispersed in a solution of a biodegradable polymer (PLGA) in a volatile water-immiscible organic solvent. The obtained "water-in-oil (w/o) emulsion" is dispersed in a continuous external water phase containing surfactant to form "water-in oil-in water (w/o/w) double emulsion" droplets. The organic solvent is slowly evaporated by stirring the double emulsion in a fume hood. The resulting microparticles are collected by filtration or centrifugation, washed with water and lyophilized. The solvents used in the aforementioned process are halogenated hydrocarbons, particularly chloroform or dichloromethane, which act as solvents for the polymer. The presence of residual, but detectable, halogenated hydrocarbon solvents in the final product, however, is undesirable, because of their general toxicity and possible carcinogenic activity. To address this, regulatory agencies have imposed limitations on the amount of residual organic solvents present in pharmaceutical compositions intended for human and veterinary uses.

There is a need in the art for an improved and reliable process for preparing microparticles containing glatiramer acetate having low levels of residual organic solvent(s), in particular halogenated organic solvents.

SUMMARY OF THE INVENTION

The present invention provides an improved process for preparing microparticles containing glatiramer acetate having low levels of residual organic solvent(s), in particular halogenated hydrocarbons such as dichloromethane. Unexpectedly it has been discovered that organic solvent levels may be reduced to regulatory-acceptable levels (e.g., less than about 600 ppm for dichloromethane) by altering the organic solvent evaporation step in the double emulsification process previously described in U.S. Pat. Nos. 8,377,885 and 8,796,226. A main challenge in modifying said process was to keep the microparticle's morphology, the binding percentage and the release profile of the glatiramer acetate active ingredient intact, despite the process modifications. It has now been discovered that application of vacuum and/or air stream to the double water-in-oil-in-water double emulsion results in a product having reduced levels of organic solvent, while still maintaining intact microparticles of glatiramer acetate. In particular, by careful adjustment of the mixing, air bubbling and/or vacuum intensities, microparticles were achieved having desired morphological and therapeutic properties (e.g., drug release profile), while at the same time minimizing the level of organic solvent to regulatory acceptable levels. For example, for chlorinated organic solvents such as dichloromethane (DCM, also referred to interchangeably as methylene chloride), the regulatory limits according to ICH guidelines are 600 ppm.

Thus, the present invention provides a process for preparing microparticles comprising glatiramer acetate, the process comprising the steps of: (a) preparing an internal aqueous phase comprising glatiramer acetate and water; (b) preparing an organic phase comprising a biodegradable or non-biodegradable polymer and a water-immiscible volatile organic solvent; (c) preparing an external aqueous phase comprising water and a surfactant; (d) mixing the internal aqueous phase obtained in step (a) and the organic phase obtained in step (b) to form a water-in-oil (w/o) emulsion; (e) mixing the water-in-oil (w/o) emulsion obtained in step (d) with the external water phase obtained in step (c) to obtain a water-in-oil-in-water (w/o/w) double emulsion; (f) removing the organic solvent by mixing the water-in-oil-in-water (w/o/w) double emulsion obtained in step (e), and applying an air stream and/or a vacuum; and (g) drying to obtain microparticles of glatiramer acetate, the microparticles comprising less than about 1,000 ppm of residual organic solvent. In one embodiment, step (f) is conducted under conditions sufficient to reduce the level of organic solvent to less than about 1,000 ppm, preferably less than about 600 ppm.

As contemplated herein, the process of the present invention results in a product having reduced levels of residual organic solvent(s), thereby being compliant with regulatory imposed limitations. In one embodiment, the microparticles comprise less than about 600 ppm residual organic solvent, which is the regulatory limit for chlorinated solvents such as DCM according to ICH guidelines. In another embodiment, the microparticles comprise less than about 500 ppm residual organic solvent. In another embodiment, the microparticles comprise less than about 250 ppm residual organic solvent. In yet another embodiment, the microparticles comprise less than about 100 ppm of residual organic solvent.

In other embodiments, the microparticles comprise less than about 0.1% of residual organic solvent(s). In another embodiment, the microparticles comprise less than about 0.05% residual organic solvent(s). In yet another embodiment, the microparticles comprise less than about 0.01% of residual organic solvent(s).

The organic solvent used in the process of the invention is water-immiscible and volatile. In some currently preferred embodiments, the organic solvent is a halogenated organic solvent such as a halogenated hydrocarbon. In some currently preferred embodiments, the chlorinated hydrocarbon is dichloromethane or chloroform, with each possibility representing a separate embodiment of the present invention.

In one particular embodiment, the process of the invention utilizes dichloromethane as an organic solvent. In accordance with this embodiment, the resulting microparticles comprise less than about 600 ppm, preferably less than about 500 ppm, less than about 250 ppm or less than about 100 ppm of residual dichloromethane.

The solvent removal step (f) comprises a combination of mixing and application of an air stream and/or vacuum to the water-in-oil-in-water (w/o/w) double emulsion. The mixing, application of air stream and/or vacuum are conducted under suitable conditions that will not affect that integrity of the final product (e.g., its morphology, GA binding percentage or release profile), while still giving rise to a product having low levels of organic solvent, as described herein.

In some embodiments, the w/o/w double emulsion may be mixed using a homogenizer, preferably at a speed of at least about 2,500 rounds per minute (RPM), preferably at least about 2,750 RPM. In some embodiments, step (f) comprises mixing the w/o/w double emulsion in combination with application of a vacuum. Preferably, the vacuum is applied for at least about 3 hours, or at least about 5 hours. In other embodiments, step (f) comprises mixing of the w/o/w double emulsion in combination with applying a compressed air stream to the w/o/w double emulsion at a pressure of about 0.1 to 1 bar, preferably about 0.5 bar or any value inbetween. In yet other embodiments, step (f) comprises mixing of the w/o/w double emulsion together with applying a combination of compressed air stream and vacuum as described above.

After solvent evaporation, the glatiramer acetate microparticles are isolated by drying (step (g)). In some embodiments, this step comprises drying the obtained microparticles into bulk or unit dose preparation. The drying may be performed by any method known in the art, for example lyophilization or freeze-drying or any other suitable drying method. In other embodiments, the process further includes a step of filtering or centrifuging the product of step (f), optionally washing with water, prior to drying, thereby obtaining the microparticles of glatiramer acetate. The polymer used in the organic phase may be biodegradable or non-biodegradable. In some embodiments, the biodegradable or non-biodegradable polymer is selected from the group consisting of poly(D,L, lactic acid) (PLA), polyglycolides (PGA), poly(lactide-co-glycolide) (PLGA) polycaprolactone, polyhydroxybutyrate, polyorthoesters, polyalkaneanhydrides, gelatin, collagen, oxidized cellulose, and polyphosphazene, with each possibility representing a separate embodiment of the present invention. In some currently preferred embodiments, the polymer is a biodegradable polymer selected from the group consisting of PLA, PGA and PLGA. A currently preferred biodegradable polymer is PLGA.

In additional embodiments, the external aqueous phase comprises a surfactant selected from polyvinyl alcohol (PVA), partially hydrolyzed polyvinyl alcohol (PVA), polysorbate, polyethylene oxide-polypropylene oxide block copolymers and cellulose esters. Each possibility represents a separate embodiment of the invention. In a currently preferred embodiments, the surfactant is PVA or partially hydrolyzed PVA.

In further embodiments, the composition further comprises a tonicity modifier. A preferred tonicity modifier is sodium chloride which is added to one or more of the aqueous phases, for creation of osmotic balance. Other suitable tonicity modifiers are described in the detailed description hereinbelow.

According to some embodiments, the glatiramer acetate comprises the acetate salt of L-alanine, L-glutamic acid, L-lysine, and L-tyrosine in the molar ratios of about 0.14 glutamic acid, about 0.43 alanine, about 0.10 tyrosine and about 0.33 lysine.

According to other embodiments, the glatiramer acetate or other pharmaceutically acceptable salt of glatiramer comprises about 15 to about 100 amino acids.

In some embodiments the microparticles comprise from about 20 mg to about 750 mg glatiramer acetate. In other embodiments, the microparticles comprise about 40 mg glatiramer acetate. In other embodiments, the microparticles comprise about 80 mg glatiramer acetate.

As contemplated herein, the glatiramer acetate microparticles are prepared in the form of a depot formulation, suitable for subcutaneous or intramuscular implantation at a medically acceptable location in a subject in need thereof. Thus, in some embodiments, the present invention relates to a long acting parenteral pharmaceutical composition comprising a therapeutically effective amount of glatiramer acetate, the composition being in a sustained release depot form suitable for subcutaneous or intramuscular implantation at a medically acceptable location in a subject in need thereof, the composition comprising microparticles of glatiramer acetate prepared in accordance with the process of the invention.

According to some embodiments, the long acting depot is suitable for a dosing schedule from about once weekly to about once in every 6 months. According to particular embodiments, the composition is suitable for dosing from about once every 2 weeks to about once monthly.

According to other embodiments, the long acting depot releases a therapeutically effective amount of glatiramer acetate over a period of about 1 week to about 6 months. According to other embodiments, the long acting depot releases a therapeutically effective amount of glatiramer acetate over a period of about 2 weeks to about 1 month. Specific examples of the long acting compositions include biodegradable or non-biodegradable microspheres, implants of any suitable geometric shape, implantable rods, implantable capsules, implantable rings, prolonged release gels and erodible matrices. Each possibility represents a separate embodiment of the invention.

The present invention further provides a method of treating multiple sclerosis, comprising the parenteral administration or implantation of a depot composition comprising a therapeutically effective amount of glatiramer acetate, the composition being prepared in accordance with the process of the present invention.

Advantageously, the pharmaceutical compositions provide equal or superior therapeutic efficacy to the commercially available daily injectable dosage forms, with reduced incidence and/or severity of side effects at the local and/or systemic levels.

The present invention encompasses a composition comprising glatiramer acetate in depot form prepared by the process according to the present invention, the depot formulation being suitable for implantation into an individual in need thereof, for use in treating multiple sclerosis, in particular relapsing-remitting multiple sclerosis (RRMS).

The present invention further encompasses the use of the implantable depot of glatiramer acetate prepared in accordance with the process of the present invention, the depot being suitable for providing prolonged release or prolonged action of glatiramer in a subject.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides an improved process for preparing microparticles containing glatiramer acetate having low levels of residual organic solvent(s), in particular dichloromethane. The microparticles are in the form of a depot formulation which may be administered by parenteral administration (e.g., intramuscularly or subcutaneously), and affords equal or superior therapeutic efficacy compared with daily Copaxone® injections and thus result in improved patient compliance. In addition to providing similar therapeutic efficacy and reduced side effects, the long acting depot compositions contain low levels or residual organic solvent (e.g., dichloromethane), thereby complying with regulatory requirements regarding permitted residual amounts of such solvents.

The microparticulate compositions of the present invention comprise a water-in oil-in water (w/o/w) double emulsion. The double emulsion comprises an internal aqueous phase comprising glatiramer acetate, an oil phase or water-immiscible organic phase comprising a biodegradable or non-biodegradable polymer and a water-immiscible organic solvent, and an external aqueous phase comprising a surfactant and optionally a tonicity modifier. The terms "oil phase" and "water-immiscible organic phase" may be used interchangeably herein.

Preparation of Microparticles

The compositions of the present invention can be prepared in the form of injectable microparticles by a process known as a "double emulsification" process, which represents an improvement of the process described in U.S. Pat. Nos. 8,377,885 and 8,796,226. According to the principles of the present invention, a solution of glatiramer acetate is dispersed in a solution of a biodegradable or non-biodegradable polymer in water-immiscible volatile organic solvent. The thus obtained "water-in-oil (w/o) emulsion" is then dispersed in a continuous external water phase containing surfactant to form "water-in oil-in water (w/o/w) double emulsion" droplets. The organic solvent is then removed (i.e., evaporated) by mixing the water-in-oil-in-water (w/o/w) double emulsion and applying an air stream and/or a vacuum, under conditions sufficient to reduce the amount of organic solvent to levels acceptable for pharmaceutical applications (e.g., compliance with ICH guidelines). The process described in U.S. Pat. Nos. 8,377,885 and 8,796,226 does not contemplate application of an air stream or a vacuum during the solvent evaporation step. In some embodiments, the level of residual organic solvent is reduced to less than the maximal residual solvent permitted according to regulatory agencies. Generally, the level of residual organic solvent is reduced to less than about 1,000 ppm. When halogenated organic solvents (e.g., dichloromethane) are used, the level is preferably reduced to less than about 600 ppm, which is the maximal regulatory allowed level. After evaporation of the organic solvent, the microparticles solidify and are collected by filtration or centrifugation. The collected microparticles (MPs) are washed with purified water to eliminate most of the surfactant and non-bonded peptide and centrifuged again. The washed MPs are collected and lyophilized without additives or with the addition of cryoprotectant (e.g., mannitol) to facilitate their subsequent reconstitution. Surprisingly, utilizing the process of the present invention, glatiramer acetate microparticles are obtain that retain the microparticles' desired properties such as morphology, binding percentage ("potency") and release profile, while still achieving reduced levels of organic solvents.

According to the present invention, glatiramer acetate microparticles are prepared by a process comprising the steps of: (a) preparing an internal aqueous phase comprising glatiramer acetate and water; (b) preparing an organic phase comprising a biodegradable or non-biodegradable polymer and a water-immiscible volatile organic solvent; (c) preparing an external aqueous phase comprising water and a surfactant; (d) mixing the internal aqueous phase obtained in step (a) and the organic phase obtained in step (b) to form a water-in-oil (w/o) emulsion; (e) mixing the water-in-oil (w/o) emulsion obtained in step (d) with the external water phase obtained in step (c) to obtain a water-in-oil-in-water (w/o/w) double emulsion; (f) removing the organic solvent by mixing the water-in-oil-in-water (w/o/w) double emulsion obtained in step (e), and applying an air stream and/or a vacuum; and (g) drying to obtain microparticles of glatiramer acetate, the microparticles comprising less than about 1,000 ppm, preferably less than 600 ppm of residual organic solvent. In one embodiment, step (f) is conducted under conditions sufficient to reduce the level of organic solvent to less than about 1,000 ppm, preferably less than about 600 ppm.

Internal Water Phase

The internal aqueous (water) phase comprises glatiramer acetate and water, which is preferably sterile water for injection (WFI). A suitable concentration range of glatiramer acetate in the internal water phase is between about 10 mg/mL to about 150 mg/mL, or any amount in-between. For example, glatiramer acetate concentration in the internal water phase may be between 80 and 120 mg/mL, between 90 and 110 mg/mL, and so forth.

For preparation of the internal water phase, a solution containing sterile WFI and glatiramer acetate is prepared and optionally filtered.

Organic Phase (Water-Immiscible Phase)

The organic phase comprises a biodegradable or non-biodegradable polymer and an organic solvent. The organic solvent is water-immiscible and volatile. In some currently preferred embodiments, the organic solvent is a halogenated hydrocarbon. In some embodiments, the halogenated solvent is a chlorinated solvent, for example dichloromethane or chloroform. Dichloromethane is also referred to interchangeably as dichloromethane or DCM. Each possibility represents a separate embodiment of the present invention.

In one particular embodiment, the process of the invention utilizes dichloromethane as an organic solvent. Regulatory allowed amounts of this solvent in pharmaceutical compositions are about 600 ppm. Accordingly, the microparticles resulting from the process of the invention preferably comprise less than about 600 ppm dichloromethane. In preferred embodiments, the resulting microparticles comprise less than about 500 ppm, for example less than about 250 ppm or less than about 100 ppm of residual dichloromethane. Each possibility represents a separate embodiment of the present invention.

The polymer may be a biodegradable or non-biodegradable polymer, with preference given to biodegradable polymers. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as Poly(e-caprolactone) i.e. PCL (Lactel® from Durect); polyanhydrides; poly(sebacic acid) SA; poly(ricenolic acid) RA; poly(fumaric acid), FA; poly(fatty acid dimmer), FAD; poly(terephthalic acid), TA; poly(isophthalic acid), IPA; poly(p-{carboxyphenoxy}methane), CPM; poly(p-{carboxyphenoxy} propane), CPP; poly(p-{carboxyphenoxy}hexane)s CPH; polyamines, polyurethanes, polyesteramides, polyorthoesters {CHDM: cis/trans-cyclohexyl dimethanol, HD: 1,6-hexanediol. DETOU: (3,9-diethylidene-2,4,8,10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly(malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) tri-block copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof. Each possibility represents a separate embodiment of the present invention.

In some embodiments, the microparticles comprise a biodegradable polymer selected from, but not limited to, PLGA, PLA, PGA, polycaprolactone, polyhydroxybutyrate, polyorthoesters, polyalkaneanhydrides, gelatin, collagen, oxidized cellulose, polyphosphazene and the like. In other embodiments, the microparticles comprise a biodegradable polymer selected from, but not limited to, PLGA, PLA and PGA. Each possibility represents a separate embodiment of the present invention.

A currently preferred biodegradable polymer is a lactic acid-based polymer, more preferably polylactide, or poly (D, L-lactide-co-glycolide) i.e. PLGA. Preferably, the biodegradable polymer is present in an amount between about 10% to about 98% w/w of the composition. The lactic acid-based polymer has a monomer ratio of lactic acid to glycolic acid in the range of 100:0 to about 0:100, preferably about 100:0 to about 10:90 and has an average molecular weight of from about 1,000 to about 200,000 daltons. However, it is understood that the amount of biodegradable polymer is determined by parameters such as the duration of use and the like.

PLGA polymers are commercially available from multiple suppliers; Alkermes (Medisorb polymers), Absorbable Polymers International [formerly Birmingham Polymers (a Division of Durect)], Purac and Boehringer Ingelheim.

For preparation of the internal water phase, the organic solvent and polymer are mixed and optionally filtered.

External Water Phase

The external water phase comprises water and a surfactant. The water is preferably sterile WFI. The external water phase may further comprise a tonicity modifier, for maintenance of osmotic balance. A preferred tonicity modifier is sodium chloride which is added to the external water phase. Other suitable tonicity modifiers include, but are not limited to: mannitol and glucose. Each possibility represents a separate embodiment of the invention.

The surfactant in the external water phase is preferably polyvinyl alcohol (PVA). However, other surfactants can be used, for example polysorbate, polyethylene oxide-polypropylene oxide block copolymers or cellulose esters, or any of the co-surfactants described hereinbelow.

For preparation of the external water phase (step (c)), the surfactant and optional tonicity modifier are mixed in water, preferably sterile WFI, and optionally filtered. Alternatively, a solution of surfactant in water may be dispersed or dissolved in a solution of water comprising a tonicity modifier. In one embodiment of the present invention, the external water phase was prepared by preparing a partially hydrolyzed PVA solution in sterile WFI and filtering through a membrane. Separately, a solution of NaCl was prepared in sterile WFI and filtered through a membrane. The NaCl solution was added to the PVA solution to thereby form the external water phase.

Water-in-Oil (w/o) Emulsion Preparation

After preparing each of the aqueous and organic phases, the w/o emulsion is formed. For this, the internal aqueous phase and organic phase are mixed, optionally using a homogenizer or other high shear mixing method, under conditions sufficient to form the w/o emulsion. In one embodiment, the internal water phase was added to the organic phase and processed using a homogenizer equipped with a rotor stator dispersion device at 2,500-10,000 rounds per minute (RPM) for a time period ranging from 1 to 30 minutes. In one specific embodiment, the w/o emulsion was prepared by homogenizing at 7,200 RPM for 10 minutes (high shear mixing).

Water-in-Oil-in-Water (w/o/w) Double Emulsion Preparation

Next, the w/o emulsion is mixed with the external water phase to form a water-in-oil-in-water (w/o/w) double emulsion. The mixing can occur using a homogenizer or other high shear mixing method, and can be performed in one batch or in multiple batches. For example, the w/o emulsion can be added to a portion of the external water phase followed by mixing, followed by adding the rest of the external water phase. Mixing is performed as described above for the w/o emulsion. In one embodiment, the w/o/w emulsion was prepared by adding the w/o emulsion to half of the external water phase during continuous mixing of the emulsion. The w/o/w double emulsion was processed using a homogenizer equipped with a rotor stator dispersion device at 2,500-10,000 rounds per minute (RPM) for a time period ranging from 1 to 30 minutes. In one specification embodiment, the w/o/w double emulsion was prepared by homogenizing a mixture containing half of the external water phase with the organic phase at 2,900 RPM for 3 minutes, followed by adding the rest of the external water phase (quench).

Solvent Removal/Evaporation

Next, the organic solvent is removed. The solvent removal step comprises a combination of mixing and application of an air stream and/or vacuum to the water-in-oil-in-water (w/o/w) double emulsion. The mixing, application of air stream and/or vacuum are conducted under suitable conditions that will not affect that integrity of the final product, and will give rise to a product having low levels of organic solvent, as described herein.

In some embodiments, the w/o/w double emulsion may be mixed using a homogenizer or other high shear mixing methods, preferably at a speed of at least about 2,500 RPM, preferably at least about 2,750 RPM. Higher or lower mixing speeds may be used, if desired.

In some embodiments, the solvent removal step comprises mixing of the w/o/w double emulsion in combination with application of vacuum. The vacuum may be applied for the desired amount of time to achieve the desired results, i.e., removal of solvent. For example, vacuum may be applied for at least 1 hour, at least 2 hours, preferably for at least about 3 hours, at least about 5 hours, etc. Vacuum may also be applied for longer amounts of time, e.g., 12-24 hours or overnight.

In other embodiments, the solvent removal step comprises mixing of the w/o/w double emulsion in combination with applying a compressed air stream to the w/o/w double emulsion. The air stream may be applied at a pressure of about 0.1 to 1 about bar, preferably about 0.5 bar. The air stream may be applied at a higher or lower pressure, depending on the desired outcome. The air pressure may be applied for the desired period of time, e.g., 1-24 hours, 5-24 hours, 10-20 hours, 10-12 hours, and the like.

In yet other embodiments, the solvent removal step comprises mixing of the w/o/w double emulsion and applying a combination of compressed air stream and vacuum.

In some specific embodiments, the w/o/w double emulsion was mixed using a homogenizer at different speeds for 15-17 hours. Compressed air was bubbled at 0.5 Pa through the emulsion for 10-12 hours. Vacuum was applied for the portion of the process, e.g., for about 3 hours or 5 about hours.

The particle size of the "water-in oil-in water (w/o/w) double emulsion" can be determined by various parameters including, but not limited to, the amount of applied force at this step, the speed of mixing, surfactant type and concentration, etc. Suitable particle sizes range from about 1 to about 100 μm.

Separation and Washing

After solvent evaporation, the glatiramer acetate microparticles are separated from the reaction mixture. In some embodiments, this step comprises filtering or centrifuging the suspension obtained from the solvent evaporation step. Centrifugation may be performed at any speed and time that will effectuate the separation of the microparticles from the emulsion. For example, in a non-limiting example, centrifugation may be performed at a speed of 2,500 to 10,000 RPM for a time period ranging, e.g., from 5 to 30 minutes. The obtained pellet may optionally be washed with water once or multiple times. In one specific embodiment, the suspension is centrifuged at 5,300 RPM for 10 minutes. The supernatant is discarded and the pellet (sedimented microparticles) is resuspended in WFI and mixed using a magnetic stirrer. The resuspended microparticles are again centrifuged at 2,900 RPM for 10 minutes to obtain glatiramer acetate microparticles.

Drying

The washed microparticles are then dried, e.g., by lyophilization/freeze drying or other drying methods known in the art, to obtain microparticles of glatiramer acetate in bulk or unit dose preparation. Drying is effectuated for a time period and at a temperature sufficient to remove the solvents and obtain dry microparticles. For example, lyophilzation may occur at −20° C. or below for a time period ranging from 12 to 48 hours.

As contemplated herein, the process of the present invention results in a product having reduced levels of residual organic solvent(s), thereby being compliant with regulatory imposed limitations. In one embodiment, the microparticles comprise less than about 600 ppm residual organic solvent. In one embodiment, the microparticles comprise less than about 500 ppm residual organic solvent. In another embodiment, the microparticles comprise less than about 250 ppm residual organic solvent. In yet another embodiment, the microparticles comprise less than about 100 ppm of residual organic solvent. In a preferred embodiment, the organic solvent is a halogenated organic solvent, for example a chlorinated organic solvent such as dichloromethane or chloroform. In this case, the microparticles should have no more than 600 ppm residual solvent, the maximal regulatory allowed amount.

Active Ingredient

The term "glatiramer acetate" as used herein refers to a compound formerly known as Copolymer 1 that is sold under the trade name Copaxone® and consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate in Copaxone® is 5,000-9,000 daltons (FDA Copaxone® label) and the number of amino acid ranges between about 15 to about 100 amino acids. The term also refers to chemical derivatives and analogues of the compound.

Glatiramer acetate may be prepared and characterized as specified in any of U.S. Pat. Nos. 8,377,885; 8,796,226; 7,199,098; 6,620,847; 6,362,161; 6,342,476; 6,054,430; 6,048,898 and 5,981,589, the contents of each of these references are hereby incorporated in their entirety.

Depot Compositions

The microparticles prepared by the process of the present invention are preferably in the form of long acting parenteral pharmaceutical compositions comprising a therapeutically effective amount of glatiramer acetate, specifically in the form of a depot formulation suitable for subcutaneous or intramuscular implantation at a medically acceptable location in a subject in need thereof.

The term "parenteral" as used herein refers to routes selected from subcutaneous (SC), intravenous (IV), intramuscular (IM), intradermal (ID), intraperitoneal (IP) and the like.

The term "therapeutically effective amount" as used herein is intended to qualify the amount of glatiramer acetate copolymer that will achieve the goal of alleviation of the symptoms of multiple sclerosis. Suitable doses include, but are not limited to, 20-750 mg for each dosage form. However, it is understood that the amount of the glatiramer acetate copolymer administered will be determined by a physician, according to various parameters including the chosen route of administration, the age, weight, and the severity of the patient's symptoms. For example, the therapeutically effective amount of the glatiramer acetate may range from about 20-100 mg. In some embodiments, the therapeutically effective amount of glatiramer acetate in the depot formulation is 40 mg. In some embodiments, the therapeutically effective amount of glatiramer acetate in the depot formulation is 80 mg.

The term "long acting" as used herein refers to a composition which provides prolonged, sustained or extended release of the glatiramer acetate to the general systemic circulation of a subject or to local sites of action in a subject. This term may further refer to a composition which provides prolonged, sustained or extended duration of action (pharmacokinetics) of the glatiramer salt in a subject. In particular, the long acting pharmaceutical compositions provide a dosing regimen which ranges from once weekly to once every 6 months. According to currently preferable embodiments, the dosing regimen ranges from once a week, twice monthly (approximately once in every 2 weeks) to once monthly. Depending on the duration of action required, each depot or implantable device will typically contain between about 20 and 750 mg of the active ingredient, e.g., 40 mg or 80 mg, designed to be released over a period ranging from about 1 week to about 6 months, e.g., from about 2 weeks to about 1 month.

The present invention further provides a method of treating multiple sclerosis by parenteral administration of a long acting pharmaceutical composition comprising a therapeutically effective amount of glatiramer acetate to a subject in need thereof, wherein the pharmaceutical composition is prepared in accordance with the process of the present invention, and comprises reduced levels of organic solvent as described herein. The term "treating" as used herein refers to suppression or alleviation of symptoms after the onset of multiple sclerosis. Common symptoms after the onset of multiple sclerosis include, but are not limited to, reduced or loss of vision, stumbling and uneven gait, slurred speech, as well as urinary frequency and incontinence. In addition, multiple sclerosis can cause mood changes and depression, muscle spasms and severe paralysis. The "subject" to which the drug is administered is a mammal, preferably, but not limited to, a human. The term "multiple sclerosis" as used herein refers to an auto-immune disease of the central nervous system which is accompanied by one or more of the symptoms described hereinabove.

The present invention provides further provides a method of alleviating at least one symptom of relapsing-remitting multiple sclerosis (RRMS) in a patient suffering from RRMS, comprising administering to the patient a long acting pharmaceutical composition comprising a therapeutically effective amount of glatiramer acetate, wherein the pharmaceutical composition is prepared in accordance with the process of the present invention, and comprises reduced levels of organic solvent as described herein.

The present invention further provides, in another aspect, a method of increasing the tolerability of GA treatment in a human patient suffering from relapsing-remitting multiple sclerosis (RRMS), comprising administering to the patient a long acting pharmaceutical composition comprising a therapeutically effective amount of glatiramer acetate, wherein the pharmaceutical composition is prepared in accordance with the process of the present invention, and comprises reduced levels of organic solvent as described herein.

The present invention further provides, in another aspect, a method of reducing the frequency of relapses in a human patient suffering from relapsing-remitting multiple sclerosis (RRMS), comprising administering to the patient a long acting pharmaceutical composition comprising a therapeutically effective amount of glatiramer acetate, wherein the pharmaceutical composition is prepared in accordance with the process of the present invention, and comprises reduced levels of organic solvent as described herein.

The present invention further provides, in another aspect, a method of preventing or slowing progression of relapsing-remitting multiple sclerosis (RRMS) in a human patient suffering from RRMS, comprising administering to the patient a long acting pharmaceutical composition comprising a therapeutically effective amount of glatiramer acetate, wherein the pharmaceutical composition is prepared in accordance with the process of the present invention, and comprises reduced levels of organic solvent as described herein.

The depot compositions may further comprise one or more pharmaceutically acceptable excipient(s) selected from, but not limited to, co-surfactants, solvents/co-solvents, water-immiscible solvents, water, water miscible solvents, oily components, hydrophilic solvents, emulsifiers, preservatives, antioxidants, anti-foaming agents, stabilizers, buffering agents, pH adjusting agents, osmotic agents, channel forming agents, osmotic adjustment agents, or any other excipient known in the art. Suitable co-surfactants include, but are not limited to, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Suitable solvents/co-solvents include, but not limited to, alcohols, triacetin, dimethyl isosorbide, glycofurol, propylene carbonate, water, dimethyl acetamide, and the like or mixtures thereof. Suitable anti-foaming agents include, but are not limited to, silicon emulsions or sorbitan sesquioleate. Suitable stabilizers to prevent or reduce the deterioration of the components in the compositions include, but are not limited to, antioxidants such as glycine, α-tocopherol or ascorbate, BHA, BHT, and the like or mixtures thereof. Suitable tonicity modifiers include, but are not limited to, mannitol, sodium chloride, and glucose. Suitable buffering agents include, but are not limited to, acetates, phosphates, and citrates with suitable cations.

The depot systems encompass any forms known to a person of skill in the art. Suitable forms include, but are not limited to, biodegradable or non-biodegradable microspheres, implantable rods, implantable capsules, and implantable rings. Further contemplated are prolonged release gel depot and erodible matrices. Suitable implantable systems are described for example in US 2008/0063687, the content of which is hereby incorporated in its entirety. Implantable rods can be prepared as is known in the art using suitable micro-extruders.

In some embodiment, the long acting pharmaceutical compositions described herein provide equal or superior therapeutic efficacy to the commercially available daily injectable dosage forms, with reduced incidence of side effects and with reduced severity of side effects at the local and/or systemic level. In some embodiments, the compositions provide prolonged release or prolonged action of glatiramer in a subject as compared to a substantially similar dose of an immediate release formulation of glatiramer acetate.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1: Preparation of PLGA Based Depot Microparticles of Glatiramer Acetate Containing Low Levels of Dichloromethane

TABLE 1

Raw materials and role

| Ingredient | Manufacturer | Role in Formulation | Composition [%] | Net Amount from Total Weight [g] |
|---|---|---|---|---|
| Sodium Chloride | SAFC | Creation of osmotic balance | 0.75 | 460 |
| Polyvinyl Alcohol | J. T. Baker | Surfactant | 0.45 | 275 |
| Dichloromethane (DCM) | Merck | Solvent of organic phase | 8.11 | 4,950 |
| Poly(Lactide-co-Glycolide) | Evonik | Polymer enclosing API | 0.90 | 550 |
| Water for Injection | B. Braun/Baxter | Solvent of internal and external phases | 89.69 | 54,745 |
| Glatiramer* Acetate | In house | API | 0.09 | 55 |

*Manufactured according to the process of U.S. Pat. No. 7,199,098.

Preparation Process (1) External water phase preparation: Partially hydrolyzed polyvinyl alcohol (PVA) solution at a concentration of 2% w/w in sterile WFI was prepared in a reactor and filtered through a 0.22 µm membrane. A solution of NaCl in sterile WFI was prepared and filtered through a 0.22 µm membrane into the reactor containing the PVA.

(3) Organic phase preparation: Organic phase composed of dichloromethane and poly(lactide-co-glycolide) was prepared in a reactor and filtered through a 0.22 µm membrane.

(4) Internal water phase preparation: A solution containing sterile WFI and glatiramer acetate was prepared and filtered through a 0.22 µm membrane.

(5) Water-in-oil (w/o) emulsion preparation: Internal water phase was added to the organic phase and processed using IKA Ultra-Turrax T50 homogenizer equipped with a rotor stator dispersion device at 7,200 RPM for 10 minutes (high shear mixing).

(6) Water-in-oil-in-water (w/o/w) emulsion preparation: Water in oil emulsion (w/o) prepared in step 5 was added to half of the external water phase during continuing mixing of the w/o emulsion. The w/o/w double emulsion was processed using IKA Ultra-Turrax UTS80 homogenizer with a rotor stator head at 2,900 RPM for 3 minutes from the end of w/o transfer into the external water phase. Following, another 30 liters of the external water phase was added to the emulsion (quench).

(7) Solvent removal/evaporation: The w/o/w double emulsion formed in step (6) was mixed using the IKA UTS80 homogenizer at different speeds for 15-17 hours. Compressed air was bubbled at 0.5 Pa through the emulsion for 10-12 hours. Vacuum was applied for the portion of the process.

(8) Separation and washing: The suspension was centrifuged at 5,300 RPM for 10 minutes. The supernatant was discarded and the pellet (sedimented microparticles) is resuspended in 550 g WFI and mixed using a magnetic stirrer for 3 minutes. The resuspended microparticles were centrifuged at 2900 RPM for 10 minutes.

(9) Drying by Lyophilization: The washed microparticles were resuspended in about 750 g sterile WFI and are kept at −20° C. until lyophilization. Lyophilization was carried out using sterile lyoguard trays as follows: Freeze at −40° C., 24 hours. Primary drying at 0.2 hPa, −5° C., 48 hours. Secondary drying at 0.2 hPa, 10° C., 48 hours.

The dry GA depot composition is provided Table 2:

TABLE 2

GA Depot 40 mg Composition per Vial

| Ingredient | mg/vial# | Function |
|---|---|---|
| GA | 44 | Active |
| POLYGLACTIN 50:50, molecular weight 7,000-17,000 (PLGA) | 506 | Carrier |
| Water for Injection* | — | Compounding solvent |
| Dichloromethane (DCM)* | — | Compounding solvent |
| Polyvinylalcohol** | — | surfactant |
| NaCl** | — | Isotonic pressure |

*Evaporated during lyophilization process
**Removed during production, does not incorporate into final product
Each vial contain 10% overage to compensate for losses during withdrawal of the reconstituted product A summary of the procedure, equipment and materials involved in the preparation of GA Depot 55 g using the 100 L reactor system is depicted in Table 3:

TABLE 3

| Stage | Composition | Vessels and Instruments |
|---|---|---|
| External Water Phase | 13750 g PVA 2% solution 460 g NaCl 40845 g WFI | 30 L glass reactor filtered through 0.2 µm aqueous membrane. |
| Internal water phase | 55 g GA (absent in placebo) 425 g WFI | 2 L glass bottle filtered through 0.2 µm aqueous membrane. |
| Organic phase | 550 g PLGA 4950 g DCM | 10 L glass reactor filtered through |

TABLE 3-continued

| Stage | Composition | Vessels and Instruments |
|---|---|---|
| Water in oil emulsification | Internal water phase is added to organic phase and processed at 7200 RPM for 10 minutes | 0.2 µm organic membrane. Homogenized in 10 L SS reactor using IKA Ultra-Turrax T50 homogenizer. |
| Water in oil in water emulsification | Water in oil emulsion is added to external water phase and processed at 2900 RPM for 3 minutes. | Homogenized in 100 L SS reactor using IKA Ultra-Turrax UTS80 homogenizer. |
| Evaporation of DCM | Mixing of double emulsion and bubbling of compressed air overnight followed by vacuum for 5 hours | Evaporation in 100 L SS reactor using IKA Ultra-Turrax UTS80 homogenizer. |
| Separation and washing | Centrifugation at 5300 RPM and 2900 RPM for 10 minutes. | Thermo Fisher Scientific RC 12BP+ centrifuge |
| Re-suspension | Dispersion of precipitate with 550 g WFI | NA |

Results and Discussion

DCM residual content: Table 4 details evaporation speed, duration of vacuum application, and DCM residual content of eight batches prepared. The results show that DCM residual content in the final formulation of GA Depot decreases by increasing evaporation speed and time of vacuum. Residual DCM complied with the limits at a speed of 2,750 RPM and 5 hours of vacuum as implemented in placebo batch (6). Two additional batches, (7, placebo)) and (8 (glatiramer acetate)) were prepared under the same evaporation conditions in order to ensure reproducibility.

TABLE 4

| Product | Batch No. | Evaporation Speed [RPM] | Pressure of Compressed Air [bar] | Time of Vacuum [hr] | DCM Residual Content [ppm] |
|---|---|---|---|---|---|
| Placebo for GA Depot 55 g | (1) | 900 | 0.5 | Vacuum was not applied | 5761 |
| | (2) | 800 | | | NA |
| | (3) | 2100 | | | 3872 |
| | (4) | 2216 | | | 1921 |
| | (5) | 2500 | | 3 | 945 |
| | (6) | 2750 | | 5 | 213 |
| | (7) | 2750 | | 5 | 82 |
| GA Depot 55 g | (8) | 2750 | | 5 | 92 |

Sterility and bacterial endotoxins: The first four placebo batches were not prepared aseptically and hence sterility and bacterial endotoxin data are not relevant. The subsequent batches were proven sterile and fall within bacterial endotoxin limitation as can be seen in Table 5 below.

TABLE 5

| Product | Batch No. | Sterility | Bacterial Endotoxins ≤ 0.3 EU/mg |
|---|---|---|---|
| Placebo for GA Depot 55 g | (1) | Not Applicable | Not Applicable |
| | (2) | | |
| | (3) | | |
| | (4) | | |
| | (5) | No growth | <0.05 |
| | (6) | No growth | 0.1904 |
| | (7) | No growth | <0.05 |
| GA Depot 55 g | (8) | No growth | 0.1303 |

In Vitro Release Profile

The in vitro system is as described in U.S. Pat. Nos. 8,377,885 and 8,796,226 as summarized below:

Materials and Methods

Equipment 20 ml vials multi-point magnetic stirrer

Incubator

Pipettors

UV-Vis spectrophotometer Shimadzu 1601

Reagents and plastic/glassware

Test-articles: Dry lyophilized microparticles containing glatiramer acetate made by the process of the invention (batch 9) or according to the process of U.S. Pat. Nos. 8,377,885 and 8,796,226 (batch 10).

Temperature: 37° C. 2,4,6-trinitrobenzenesulfonic acid (TNBS, picrylsulfonic acid, 170.5 mM) 5% in MeOH Process description: 20 ml of PBS (0.01M phosphate, 0.05% $NaN_3$) pH 7.4 were added to each vial. The vials were placed at 37° C. and stirred with a small magnet. 600 µl samples were centrifuged at 10,000 g for 5 minutes. 500 µl of supernatant were transferred to a 1.5 ml microtube followed by the addition of 500 µl of 0.1M borate buffer (2-fold dilution) and 50 µl TNBS. The resulting composition was mixed and was kept on the bench for 30 minutes. Analysis was performed using TNBS method (described below).

The remaining precipitated particles, re-suspended with 500 µl of fresh PBS (with $NaN_3$), were returned to the vial. Correct calculation for released amount of glatiramer acetate was performed in a further release process for 2.5% for each time-point.

The release of the incorporated glatiramer acetate was carried out in tightly closed 20 ml glass vials, using incubator at 37° C., equipped with a multi-point magnetic stirrer. Phosphate buffered saline (PBS) with pH 7.4 was used as a release media.

The release of the glatiramer acetate was tested over a period of 1-30 days. The content of GA released is determined by a GPC method Instrument: Suitable HPLC system equipped with a UV detector Column: Superose 12 HR 10/30 column Detection: UV at 208 nm Flow rate: 0.5 ml/min Injection volume: 10 µL Column temperature: ambient Mobile phase: 0.2M phosphate buffer pH 1.5

A representative release profile of two representative samples of GA depot made by the process of the invention are provided in Table 6.

TABLE 6

Release profile of 100L GA Depot, two representative batches, batch (9) made by the process of the invention, in comparison to batch (10) according to the process described in U.S. Pat. No. 8,377,885 and U.S. Pat. No. 8,796,226.

| Batch number | 9 | 10 |
| --- | --- | --- |
| day 0 | 11% | NT |
| day 1 | 13% | 10% |
| day 7 | 19% | 22% |
| day 14 | 43% | 35% |
| day 21 | 80% | 68% |
| day 30 | 98% | 93% |

CONCLUSIONS

As demonstrated herein, it can be concluded that by increasing evaporation speed followed by the application of vacuum it was possible to optimize DCM evaporation and acquire results which fall within the required specifications. The results show that the optimal evaporation conditions are a homogenization speed of about 2,750 RPM and about 5 hours of vacuum. Surprisingly, minimization of DCM levels was achievable utilizing the process of the invention, while still maintaining the desired product attributes (GA binding percentage, particle morphology and release profile of the glatiramer acetate active ingredient remained intact despite the process modifications).

Furthermore, the batches were tested for bacterial endotoxins and sterility, which also conformed to their acceptance criteria.

Example 2: Comparative Experiment

GA Depot was prepared according to the process described in Example 3 of WO 2011/080733 (corresponding to U.S. Pat. Nos. 8,377,885 and 8,796,226). For solvent (DCM) removal, an open beaker containing the double emulsion was placed on a magnetic plate stirrer and stirred for 3-4 hours at room temperature in a fume hood until all solvent evaporated and the microparticles had solidified. No air stream and/or vacuum was applied.

Lyophilized samples were tested for DCM levels using headspace GC. Average amount of DCM detected in the samples was 19,453 ppm.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A process for preparing microparticles comprising glatiramer acetate, the process comprising the steps of:
   a. preparing an internal aqueous phase comprising glatiramer acetate and water;
   b. preparing an organic phase comprising a biodegradable or non-biodegradable polymer and a water-immiscible volatile organic solvent;
   c. preparing an external aqueous phase comprising water and a surfactant;
   d. mixing the internal aqueous phase obtained in step (a) and the organic phase obtained in step (b) to form a water-in-oil (w/o) emulsion;
   e. mixing the water-in-oil (w/o) emulsion obtained in step (d) with the external water phase obtained in step (c) to obtain a water-in-oil-in-water (w/o/w) double emulsion;
   f. removing the organic solvent by mixing the water-in-oil-in-water (w/o/w) double emulsion obtained in step (e), and applying a compressed air stream and a vacuum, wherein the compressed air stream is applied at a pressure of about 0.1 to 1 bar, and wherein the vacuum is applied for at least about 3 hours; and
   g. drying to obtain microparticles of glatiramer acetate, said microparticles comprising less than about 1,000 ppm of residual organic solvent.

2. The process according to claim 1, wherein the microparticles comprise less than about 600 ppm of residual organic solvent.

3. The process according to claim 1, wherein the water-immiscible volatile organic solvent is a halogenated organic solvent.

4. The process according to claim 3, wherein the halogenated organic solvent is a chlorinated hydrocarbon selected from the group consisting of dichloromethane (DCM) and chloroform.

5. The process according to claim 4, wherein the microparticles comprise less than about 600 ppm of residual dichloromethane (DCM).

6. The process according to claim 1, wherein step (f) comprises mixing the w/o/w double emulsion in a homogenizer at a speed of at least about 2,500 rounds per minute (RPM).

7. The process according to claim 1, wherein step (f) comprises applying vacuum to the w/o/w double emulsion for at least about 5 hours.

8. The process according to claim 1, wherein step (f) comprises mixing the w/o/w double emulsion in a homogenizer at a speed of at least about 2,750 RPM, applying a compressed air stream at a pressure of about 0.5 bar, and applying vacuum for at least about 5 hours.

9. The process according to claim 1, further comprising the step of filtering or centrifuging the product of step (f) and optionally washing with water prior to the drying step (g).

10. The process according to claim 1, wherein the drying step (g) comprises lyophilization or freeze-drying.

11. The process according to claim 1, wherein the biodegradable or non-biodegradable polymer is selected from the group consisting of poly(D,L, lactic acid) (PLA), polyglycolides (PGA), poly(lactide-co-glycolide) (PLGA) polycaprolactone, polyhydroxybutyrate, polyorthoesters, polyalkaneanhydrides, gelatin, collagen, oxidized cellulose, and polyphosphazene.

12. The process according to claim 1, wherein the surfactant in the external water phase obtained in step (c) is selected from the group consisting of polyvinyl alcohol (PVA), partially hydrolyzed polyvinyl alcohol (PVA), polysorbate, polyethylene oxide-polypropylene oxide block copolymers and cellulose esters.

13. The process according to claim 1, wherein the glatiramer acetate microparticles are in the form of a long acting parenteral pharmaceutical composition in sustained release depot form suitable for subcutaneous or intramuscular implantation at a medically acceptable location in a subject in need thereof.

14. The process according to claim 1, wherein the microparticles comprise from about 20 mg to about 750 mg glatiramer acetate.

15. A long acting parenteral pharmaceutical composition comprising a therapeutically effective amount of glatiramer acetate, the composition being in a sustained release depot form suitable for subcutaneous or intramuscular implantation at a medically acceptable location in a subject in need thereof, the composition comprising microparticles of glatiramer acetate prepared in accordance with the process of claim 1.

16. The pharmaceutical composition according to claim 15, wherein the depot composition releases a therapeutically effective amount of glatiramer acetate over a period of about 1 week to about 6 months.

17. The pharmaceutical composition according to claim 15, wherein the depot composition releases a therapeutically effective amount of glatiramer acetate over a period of about 2 weeks to about 1 month.

18. A method of treating multiple sclerosis by parenteral administration of the glatiramer acetate microparticles prepared in accordance with the process of claim 1, or a pharmaceutical composition in depot form comprising such microparticles.

19. The method of claim 18, wherein the multiple sclerosis is relapsing-remitting multiple sclerosis (RRMS).

* * * * *

UNITED STATES PATENT AND TRADEMARK OFFICE
CERTIFICATE OF CORRECTION

PATENT NO. : 11,471,421 B2
APPLICATION NO. : 16/328572
DATED : October 18, 2022
INVENTOR(S) : Nadav Bleich Kimelman et al.

It is certified that error appears in the above-identified patent and that said Letters Patent is hereby corrected as shown below:

In the Specification

In Column 9, Line 61, replace "Compressed air was bubbled at 0.5 Pa" with --Compressed air was bubbled at 0.5 Bar--; and
In Column 14, Line 18, replace "Compressed air was bubbled at 0.5 Pa" with --Compressed air was bubbled at 0.5 Bar--.

Signed and Sealed this
Twentieth Day of December, 2022

Katherine Kelly Vidal
*Director of the United States Patent and Trademark Office*